United States Patent
McLean et al.

(10) Patent No.: US 6,986,792 B2
(45) Date of Patent: Jan. 17, 2006

(54) PROSTHESES

(75) Inventors: Terry McLean, Cordova, TN (US); Richard Lambert, Germantown, TN (US); David Kelman, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 10/243,502

(22) Filed: Sep. 13, 2002

(65) Prior Publication Data

US 2004/0054418 A1    Mar. 18, 2004

(51) Int. Cl.
A61F 2/32    (2006.01)

(52) U.S. Cl. .................. 623/22.29; 623/22.19; 623/22.2; 623/22.28

(58) Field of Classification Search .. 623/19.11–19.14, 623/22.11, 22.17–22.2, 22.28, 22.29, 22.3, 623/18.11
See application file for complete search history.

(56) References Cited

U.S. PATENT DOCUMENTS

| | | | |
|---|---|---|---|
| 3,787,128 A | | 1/1974 | Maistrelli |
| 3,813,699 A | | 6/1974 | Giliberty |
| 3,818,512 A | * | 6/1974 | Shersher .................. 623/22.15 |
| 3,862,807 A | | 1/1975 | Doden et al. |
| 3,863,273 A | | 2/1975 | Averill |
| 4,044,403 A | | 8/1977 | D'Errico |
| 4,172,296 A | | 10/1979 | D'Errico |
| 4,241,463 A | | 12/1980 | Khovaylo |
| 4,380,090 A | | 4/1983 | Ramos |
| 4,619,658 A | | 10/1986 | Pappas et al. |
| 4,624,674 A | | 11/1986 | Pappas et al. |
| 4,642,123 A | | 2/1987 | Noiles |
| 4,676,798 A | | 6/1987 | Noiles |
| 4,676,799 A | * | 6/1987 | Legrand .................. 623/22.19 |
| 4,678,472 A | | 7/1987 | Noiles |
| 4,695,282 A | | 9/1987 | Forte et al. |
| 4,718,911 A | | 1/1988 | Kenna |
| 4,729,041 A | | 3/1988 | Kuroda |
| 4,770,658 A | | 9/1988 | Geremakis |
| 4,784,663 A | | 11/1988 | Kenna |
| 4,795,471 A | | 1/1989 | Oh |

(Continued)

FOREIGN PATENT DOCUMENTS

EP    0412438 A2    2/1991

(Continued)

OTHER PUBLICATIONS

Article entitled DUOLOX®-System aus BIOLOX® forte, *CeraNews*, 1 page (Feb. 1998).

(Continued)

Primary Examiner—Bruce Snow
Assistant Examiner—Cheryl Miller
(74) Attorney, Agent, or Firm—Kilpatrick Stockton LLP (57) ABSTRACT

Bipolar prostheses which include various structures and other techniques for optimizing material wear and mechanical strength properties. Such prostheses feature, for example, improved resistance to polyethylene wear while also reducing potential for dislocation of the femoral stem from the prosthesis. Such techniques and structures include varying wear resistance and mechanical strength treatment in various components of the prostheses or portions of those components as desired to improve, accentuate or optimize wear performance and dislocation reduction, locking ring structural features, structures for retaining locking rings in the bipolar prosthesis shell, and structures for limiting or reducing movement or rotation of locking rings and liners in bipolar prosthesis shells.

6 Claims, 5 Drawing Sheets

U.S. PATENT DOCUMENTS

| | | | |
|---|---|---|---|
| 4,798,610 A | 1/1989 | Averill et al. | |
| 4,936,855 A | 6/1990 | Sherman | |
| 4,950,299 A | 8/1990 | Noiles | |
| 4,960,427 A | 10/1990 | Noiles | |
| 5,019,105 A | 5/1991 | Wiley | |
| 5,049,158 A | 9/1991 | Engelhardt et al. | |
| 5,062,853 A | 11/1991 | Fòrte | |
| 5,092,898 A * | 3/1992 | Bekki et al. | 623/22.16 |
| 5,133,763 A | 7/1992 | Mullers | |
| 5,156,626 A | 10/1992 | Broderick et al. | |
| 5,181,926 A | 1/1993 | Koch et al. | |
| 5,263,988 A | 11/1993 | Huebner | |
| 5,310,408 A | 5/1994 | Schryver et al. | |
| 5,314,491 A | 5/1994 | Thongpreda et al. | |
| 5,383,938 A | 1/1995 | Rohr et al. | |
| 5,425,778 A | 6/1995 | Zichner et al. | |
| 5,425,779 A | 6/1995 | Schlosser et al. | |
| 5,507,826 A | 4/1996 | Besselink et al. | |
| 5,549,681 A | 8/1996 | Segmuller et al. | |
| 5,725,587 A | 3/1998 | Garber | |
| 5,800,555 A | 9/1998 | Gray, III | |
| 5,824,108 A | 10/1998 | Huebner | |
| 5,879,404 A | 3/1999 | Bateman et al. | |
| 5,888,211 A | 3/1999 | Sanders | |
| 5,916,270 A | 6/1999 | Lipman | |
| 5,989,293 A * | 11/1999 | Cook et al. | 623/22.29 |
| 6,042,611 A | 3/2000 | Noiles | |
| 6,042,612 A | 3/2000 | Voydeville | |
| 6,129,765 A | 10/2000 | Lopez et al. | |
| 6,165,220 A | 12/2000 | McKellop et al. | |
| 6,206,929 B1 | 3/2001 | Ochoa et al. | |
| 6,248,132 B1 | 6/2001 | Harris | |
| 6,334,875 B1 | 1/2002 | Keller | |
| 6,365,089 B1 * | 4/2002 | Krebs et al. | 264/485 |
| 6,494,917 B1 * | 12/2002 | McKellop et al. | 623/23.58 |
| 6,527,808 B1 * | 3/2003 | Albertorio et al. | 623/22.26 |
| 2003/0050703 A1 * | 3/2003 | Harris et al. | 623/22.2 |
| 2004/0143341 A1 * | 7/2004 | McLean | 623/22.15 |
| 2004/0225369 A1 * | 11/2004 | Lakin et al. | 623/22.15 |

FOREIGN PATENT DOCUMENTS

| | | |
|---|---|---|
| EP | 0 707 838 A | 4/1996 |
| EP | 0 945 109 A | 9/1999 |
| FR | 2765100 | 12/1998 |

OTHER PUBLICATIONS

Smith & Nephew—Orthopaedics—Convene Bipolar System http://ortho.smith-nephew.com/us/Standard.asp?Nodeld=219, 1 page (Aug. 2, 2002).

Smith & Nephew—Orthopaedics—Convene® Bipolar System Surgical Techniquehttp://ortho.smith-nephew.com/us/Flash.asp?Nodeld=3155, 7 pages (Aug. 2, 2002).

Wheeless' Textbook of Orthopaedics—Bipolar Arthroplasty http://www.medmedia.com/o14/51.htm, 2 pages (Aug. 2, 2002)..

Joint Replacement—Hip Systems—Hip Heads—mathys Join Replacement http://www.mathysmedical.ch/products/ortho/hip/heads/ortho_hip_heads_cem.html, 2 pages (Aug. 2, 2002).

Plus Orthopaedics—Design Rationale—Bipolar http://www.plusortho.com/dr_bipolar.html, 3 pages (Aug. 2, 2002).

Smith & Nephew Brochure Entitled Reflection† XLPE Cross-linked Polyethylene Acetabular Liners, 16 pages (Apr. 2002).

* cited by examiner

PROSTHESES

This invention relates to improved prostheses, including bipolar prostheses, which facilitate reduction of polyethylene wear and potential of femoral/acetabular dislocation.

BACKGROUND

Major issues associated with design of prosthetic components include the need to reduce wear of the materials forming the components and the need to optimize their mechanical performance, including stability and range of motion. For instance, design of an acetabular component in a total hip replacement typically includes materials and geometry that permit adequate range of motion of the stem head in the component while at the same time reducing tendency of the head to dislocate from the component and reducing wear of the materials forming the prosthesis.

Bipolar prostheses are a nonlimiting case in point. Bipolar prostheses generally provide two bearing surfaces between the (artificial) femoral head and the acetabulum. The first bearing surface is the typically smooth outer surface of the bipolar prosthesis shell, which may be formed of metal, ceramic material or as otherwise desired. A liner, conventionally formed of polyethylene material such as ultra high molecular weight polyethylene, may be adapted to fit tightly within the shell and provide an inner bearing surface which receives and cooperates with the femoral head in an articulating relationship to track and accommodate the relative movement between the femur and the acetabulum.

This dual bearing surface design is often indicated for patients whose acetabulae are relatively healthy and able to accommodate a prosthetic proxy for the anatomical femoral head. Bipolar prostheses leverage the theory that wear and erosion of the acetabulum will be reduced where articulating motion is absorbed by two bearing surfaces rather than one, i.e., relative movement between the shell outer surface and the acetabulum on the one hand and between the femoral stem head and the prosthesis liner on the other. The dual bearing surface thus distributes shear forces between the inner and outer bearings in order to spare the acetabular surface from wear and erosion. Additionally, acetabular wear is diminished through reduction of relative motion between the acetabular anatomy and the outer surface of the prosthesis because the inner bearing formed by the liner against the femoral stem head absorbs some of the motion. Moreover, the dual bearing surfaces typically provide greater range of motion than provided by either unipolar designs or conventional total hip arthoroplasty.

Even though bipolar prostheses are well beyond the first generation of design and implementation, a number of issues remain. These include (1) the potential for dislocation of the femoral stem head relative to the shell/liner; and (2) polyethylene wear issues.

The dislocation problem is exacerbated because dislocations often require surgical intervention to reestablish the prosthetic/hip joint. Accordingly, conventional bipolar designs and other hip prosthesis designs often feature a snug fit in which the stem head is captured in the liner. Such designs include a reduced diameter liner opening through which the stem head is forced before installation of the shell/liner. Other designs feature retention rings or locking rings. However, overemphasis on dislocation prevention can reduce range of motion between the femoral stem and the shell/liner. Additionally, previous designs are limited by the extent to which the polyethylene can "stretch" to accommodate the stem head in a capture fit. Some previous locking ring designs in bipolar prostheses have accommodated the issue by including a split in the annulus formed by the locking ring so that the diameter of the locking ring may be expanded for penetration of the stem head before installation of the prosthesis, and contracted again for installation in a manner that seeks to effectively capture the stem head and thus prevent dislocation. Split rings, however, present their own sets of issues, including potential to expand and contract in diameter even after installed which can in turn introduce polyethylene wear issues in addition to unacceptable "pistoning" of the stem head in the liner with potential polyethylene wear and stability complications.

Polyethylene wear has been recognized as an undesirable effect sometimes caused by articulating and non-articulating relative motion between a polyethylene surface and another surface such as, for instance, a metal surface such as that of a bearing in a hip prosthesis. One reason that polyethylene wear is considered serious is that even a very small volume of polyethylene debris actually includes a great number of polyethylene particles. For instance, one cubic millimeter of polyethylene wear debris can include up to ten trillion polyethylene particles. These particles are believed to cause osteolysis when they escape into nearby bone and tissue. Such polyethylene wear can occur between surfaces which articulate relative to one another and also between surfaces which are intended not to articulate but only engage only in so-called "micromotion."

Various approaches have been adopted in order to reduce generation of polyethylene wear debris. These include precise and specialized finishing and treatment of the polyethylene and the metal or other surfaces which bear against the polyethylene. They also include measures to enhance wear performance of the polyethylene such as irradiation and other processes employed to increase cross-linking or other material properties in the polyethylene. While cross-linking is advantageous to enhance polyethylene wear performance, it can also reduce mechanical and physical properties of the polyethylene such as, for instance, yield strength, tensile strength, elongation and impact strength. Accordingly, while cross-linking measures are useful for reducing wear of polyethylene in bipolar prostheses, polyethylene liners and locking rings formed of cross-linked polyethylene can suffer reduced ability to capture and retain a femoral stem head in order to prevent dislocation.

SUMMARY OF THE INVENTION

Various embodiments of the present invention include various structures and techniques for reducing polyethylene wear while at the same time increasing or at least not compromising ability of the shell/liner (or simply a shell) in a prosthesis such as a hip prosthesis to reduce or prevent dislocation of the femoral stem head without undue compromise of range of motion.

According to a first group of aspects according to certain embodiments of the invention, properties of materials that form portions of a hip prosthesis, such as the shell and (if used) liner and/or locking ring can be varied. For instance, portions of a shell, liner, and/or locking ring located at predetermined locations on those components can be altered such as by treating the material at those locations, in order to improve, accentuate or optimize wear performance, while other locations can be altered, treated differently, or not treated in order to improve, accentuate or optimize other properties such as yield strength, tensile strength, elongation, and impact strength, among other properties.

As a first example, in a total hip replacement acetabular component, portions of a polyethylene liner adapted to be locked in a metallic shell could be treated to improve cross-linking or wear performance at locations deep in the liner that are expected to absorb more compressive load from the femoral head. Portions of the liner which are located closer to the lip may omit such treatment so that they feature appropriate yield strength, tensile strength, elongation properties, impact strength, and other mechanical properties that tend to aid the liner in retaining the femoral head in the liner preferably while maintaining adequate range of motion of the femoral stem relative to the acetabular component.

As a second example, in a bipolar prosthesis which includes a metallic shell with a polyethylene liner and a polyethylene retaining or locking ring, the liner may be formed of polyethylene which has been treated to improve cross linking or other properties that improve resistance to polyethylene wear, while the retaining or locking ring is not so treated, treated to a lesser extent, or otherwise treated, in order to optimize mechanical properties that help the locking ring retain the femoral head and thus prevent dislocation of the head from the bipolar prosthesis. Portions of the metallic shell and/or femoral stem head can also be made or treated in order to improve wear performance against polyethylene surfaces, including formation or treatment to impart special finishes or compositions. Thus, bipolar prosthetic and other prosthetic components which feature polyethylene treatment of the sort mentioned above or other location and/or property-sensitive polyethylene treatment as disclosed herein, can be combined with shells and/or heads on which special surfaces such as an oxidized zirconium surface has been imparted.

According to certain aspects of certain embodiments of the invention, polyethylene prosthetic components exploit properties of various types of irradiated polyethylene materials. Because it has been generally recognized that cross-linked polyethylene which has been irradiated according to conventional and other techniques exhibits improved wear performance when placed in articulating and non-articulating relationships with metal and other surfaces, certain structures and processes according to certain embodiments of the present invention optimize cross linking of various regions of the liner which are in a position to accept increased load from the femoral stem head. These portions may include some or all of the liner. On the other hand, the locking ring, or portions of it, may be formed of non or reduced cross-linked polyethylene in order to optimize properties such as yield strength, tensile strength, elongation and impact strength. The irradiation may occur according to any desired process, including irradiation of stock polyethylene material to whatever desired degree, irradiation of all or portion of components after they are formed into shape, combinations of these techniques, or as otherwise desired. Such optimized performance thus allows bipolar prostheses according to certain aspects of the present invention to minimize polyethylene wear while at the same time featuring acceptable or improved dislocation prevention, range of motion and other performance characteristics.

According to another group of aspects of certain embodiments of the present invention, various mechanical and physical structures for bipolar prostheses in particular assist in improving, accentuating or optimizing wear performance, resistance to dislocation and range of motion characteristics.

As a first example of such mechanical or physical structures, certain bipolar prosthetic structures according to certain embodiments of the present invention feature non-split locking rings which are adapted to be placed over the neck of a two-piece femoral stem before the head is mounted on the stem. The non-split locking ring thus features a substantially smaller opening diameter than the largest diameter of the femoral stem head so that it more effectively captures the head and reduces potential of dislocation. These aspects of the invention accordingly take advantage of modular hip stem designs, which allows the ring to be assembled on the stem before the head is mounted, and before the head and locking ring are then assembled into the shell or shell/liner, in order to create a tighter locking ring constriction relative to the stem head.

Such non-split locking rings can be retained in the shell/liner combination or the shell using any capture or retention component or approach, including without limitation, an interference fit, a reverse biased lip, a retention ring which is captured in a shell and captures liner lip or outer surfaces, or a spring metal retainer ring captured in an indentation or groove formed in the outer surface of the locking ring and a corresponding indentation or groove formed on the inner surface of the shell.

Additionally, the locking ring, whether split or non-split, may feature irregularities such as a peripheral tab, protrusion or indentation which corresponds with and cooperates with structure on the inner surface of the shell in order to reduce or prevent rotation of the locking ring within the shell. Such reduced rotation reduces wear of polyethylene or other material from which the locking ring is formed.

In various bipolar prosthetic structures according to certain embodiments of the present invention which include a polyethylene liner within the shell, the liner outer surface can also include an irregularity such as a ridge or an indentation which cooperates with corresponding structure on the inner surface of the shell. These surfaces can accordingly preclude or reduce rotation of the liner in a shell in order to reduce wear of the materials of which the shell and/or liner are formed.

It is accordingly an object of certain aspects of certain embodiments of the present invention to provide prostheses which enhance polyethylene wear performance properties while at the same time enhancing or not compromising ability of the prosthesis to prevent or reduce dislocation of the femoral stem.

It is an additional object of certain aspects of certain embodiments of the present invention to provide hip prostheses in which portions of a bearing surface which cooperates with a femoral stem head accentuate, improve or optimize a first set of properties such as material wear performance, and other portions of the surface accentuate, improve or optimize a second set of properties such as yield strength, tensile strength, elongation properties, and/or impact strength.

It is an additional object of certain aspects of certain embodiments of the present invention relating to hip prostheses which feature a shell and a liner, to provide a liner in which portions improve, accentuate or optimize a first set of properties such as material wear performance, and other portions improve, accentuate or optimize a second set of properties such as yield strength, tensile strength, elongation properties, and/or impact strength.

It is an additional object of certain aspects of certain embodiments of the present invention relating to hip prostheses which feature a shell, a liner and a locking ring, to provide a liner, and if desired a locking ring, in which portions improve, accentuate or optimize a first set of properties such as material wear performance, and other portions improve, accentuate or optimize a second set of properties such as yield strength, tensile strength, elongation properties, and/or impact strength.

It is an additional object of certain aspects of certain embodiments of the present invention relating to hip prostheses which feature a shell without liner, to provide a shell in which portions improve, accentuate or optimize a first set of properties such as material wear performance, and other portions improve, accentuate or optimize a second set of properties such as yield strength, tensile strength, elongation properties, and/or impact strength.

It is an additional object of certain aspects of certain embodiments of the present invention to provide bipolar hip prostheses which include a liner at least a portion of which is formed of polyethylene that enhances wear performance, and a locking ring at least a portion of which is formed of polyethylene which enhances mechanical performance properties such as yield strength, tensile strength, elongation and impact strength.

It is an additional object of certain aspects of certain embodiments of the present invention to provide bipolar prostheses with a locking ring that is designed to take advantage of two-piece femoral stem designs which permit the locking ring to be assembled onto the femoral stem before the head is mounted on the stem.

It is an additional object of certain aspects of certain embodiments of the present invention to provide bipolar prostheses which include mechanical structure to preclude or reduce relative motion between the locking ring and the shell and/or between the liner and the shell in order to reduce polyethylene wear.

It is an additional object of certain aspects of certain embodiments of the present invention to provide bipolar prostheses which employ a locking ring held in place by a retainer captured in a groove or cooperating with other structure in the outer surface of the locking ring in order to reduce relative motion between the locking ring and the shell and reduce pistoning and other undesired relative motion between the femoral stem head and the shell or liner.

Other objects, features, and advantages of the invention and certain aspects and embodiments of it will become apparent with respect to the remainder of this document.

DETAILED DESCRIPTION a. Particular Bipolar Prosthetic Structures for Improving Material Wear and Dislocation Properties.

Figure 1:
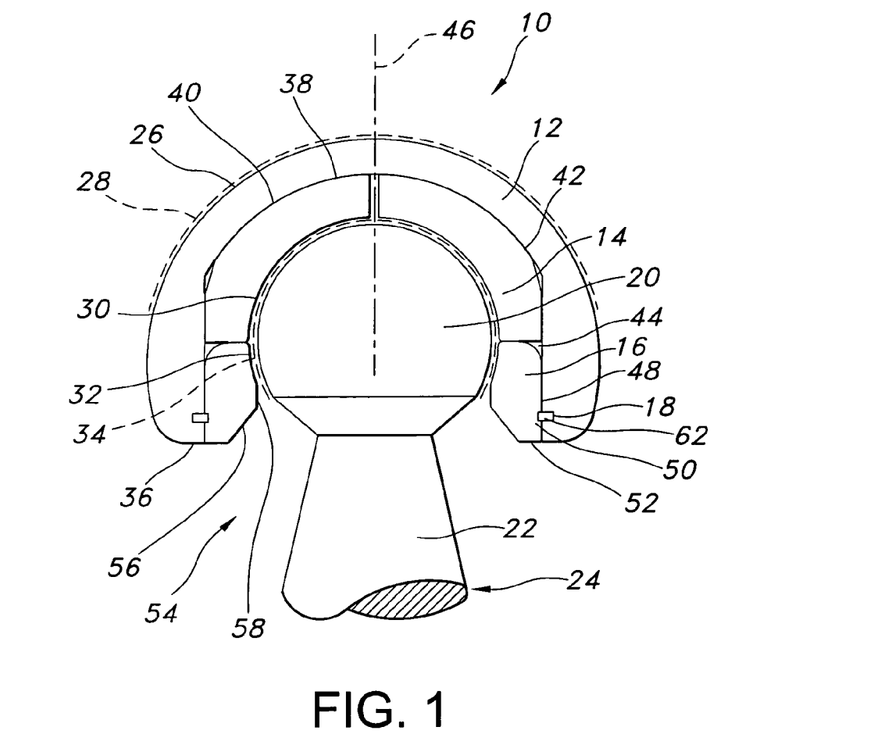
FIG. 1 shows a cross-sectional view of a preferred embodiment of a prosthesis according to certain aspects of the present invention.

For purposes of disclosing aspects and embodiments of the invention using a specific and nonlimiting example, FIG. 1 shows a cross-section of a preferred embodiment of a bipolar prosthesis 10 according to certain aspects of the present invention. Prosthesis 10 generally includes a shell 12 which receives a liner 14 and a locking ring 16 which may be held in place by a retainer 18. The prosthesis 10 is adapted to fit within and articulate, or fit in an articulating relationship with, the acetabulum. "Articulating relationship" means a physical relationship that allows relative motion or movement between two components of a prosthesis in a manner that corresponds to motion or movement of two body parts relative to each other, such as bone structure on opposing sides of a joint such as an ankle, knee, hip, wrist, elbow or shoulder. For instance, prosthesis 10 and a femoral stem it accommodates are connected in an articulating relationship, while the liner fixed within the prosthesis may not be connected in an articulating relationship with the shell. The stem and the prosthesis "articulate" relative to each other.

Prosthesis 10 is adapted to receive head 20 which is mounted (such as using a Morse taper) on neck 22 of a femoral stem 24. Femoral stem 24 and these components may be any desired conventional stem components, formed of any desired materials.

Prosthesis 10 is thus adapted to be positioned in articulating relationship relative to a patient's acetabulum and relative to femoral stem 24. The outer surface 26 of shell 12 forms an outer bearing surface which cooperates with the acetabulum tissue to form an outer bearing 28. The inner, bearing surface 30 of liner 14 and the inner, bearing surface 32 of locking ring 16 cooperate with the femoral stem head 20 to form an inner bearing 34.

Shell 12 may be formed of any desirable material conventionally used for bipolar shells, including various metallic or ceramic materials. Outer surface 26 may be finished with a mirror surface, polished, or otherwise finished for optimum articulation relative to the acetabulum. Outer surface 26 may form a portion of a sphere, an ovaloid structure or shaped as otherwise desired in order to optimize articulation while at the same time reducing potential for migration and dislocation. It may be equal to or form more or less than half of such a structure; for instance, outer surface 26 may be hemispherical, more shallow than hemispherical or deeper than hemispherical as desired.

Outer surface 26 of shell 12 may round or otherwise transition to a portal surface 36 of shell 12. Portal surface 36 as well as the transition may assume any desired shape in order to accommodate the form, function and fit of prosthesis 10.

A shell cavity 38 is formed by a shell inner surface 40. As shown in FIG. 1, a first portion of shell cavity 38 may be dome shaped, hemispherical, or otherwise formed of a surface of rotation or as otherwise desired while a second portion, closer to portal surface 36, may be cylindrical or otherwise shaped as desired. Cavity 38 is formed to accept and receive liner 14 and locking ring 16. It may be shaped and surfaced as desired in order to optimize the preferably non-articulating relationship between shell 12 and liner 14 on the one hand and shell 12 and locking ring 16 on the other hand.

Liner 14, and ring 16, or desired portions of one or both of them, may be formed of various types of polyethylene in a continuous or discontinuous fashion to improve, accentuate or optimize properties such as wear performance. For instance, all of liner 14 may be formed of highly crosslinked high-density polyethylene which has been irradiated or otherwise treated, before or after being formed into the shape that corresponds to liner 14, while all of locking ring 16 may omit such treatment in order to retain mechanical properties that help resist femoral stem dislocation, such as yield strength, tensile strength, elongation properties, and/or impact strength. Any cross-linking or wear resistance treatment of the materials from which liner 14 or locking ring 16 are made can be employed. Treatment can also occur to enhance wear performance during or after the liner 14 and/or locking ring 16 have been formed into shape. A combination of these techniques can be employed.

Alternatively, various portions of liner 14 and/or ring 16, such as those on the liner near the axis of rotation 46, and/or locations on the locking ring 16 surface which bear against the head of a femoral stem in articulating relationship can, for instance, feature polyethylene or other materials which have been treated at desired levels to improve wear resistance. Treatment may be varied according to various locations in liner 14, such as cross linking treatment being reduced gradually across the continuum that extends from the axis of rotation 46 to the liner interface surface 44. According to such wear resistance treatment, properties of various locations of liner 14 may feature improved, accentuated or optimized wear resistance, and other locations can feature improved, accentuated, or optimized mechanical properties such as yield strength, tensile strength, elongation and impact strength.

Liner 14 as shown in FIGS. 1–5 is adapted and configured to be received, preferably snugly, in non-articulating relationship with cavity 38 and shell 12. Liner 14 accordingly, in the embodiment shown in FIGS. 1–5, features an outer surface 42 with a first portion corresponding to the first portion of cavity 38 and a second portion generally corresponding to the second portion of cavity 38. An irregularity 45 such as a groove, slot, ridge or other desired structure can be formed in surface 42 in order to cooperate with corresponding structure formed on or in shell 12 to reduce or prevent rotation of liner 14 in shell 12.

Liner 14 includes a liner interface surface 44 which can, if desired, be shaped and finished to cooperate with locking ring 16 in order among other things to optimize polyethylene wear and/or constrain relative motion of liner 14 vis a vis locking ring 16 and/or shell 12.

Liner inner surface 30 is preferably hemispherical and finished as desired in order to optimize articulating and wear properties of inner bearing 34 relative to stem head 20. Inner surface 30 may feature a center of rotation which is different from the center of rotation of outer surface 26 of the shell and/or the first portion of shell cavity 38 or shell inner surface 40. Such geometry is sometimes referred to as "eccentric" and can be employed as desired and if desired in order to improve migration and/or other properties of prosthesis 10.

Locking ring 16 features an outer surface 48 which is adapted to correspond to and fit within shell cavity 38. It may be finished and shaped as desired, and it may include a non-rotational irregularity such as one or more irregularities 53 such as a tab, groove, slot, ridge or other structure which corresponds with one or more irregularities on shell inner surface 40 to reduce or prevent rotation of locking ring 16 relative to shell 12 and thus reduce polyethylene wear.

Outer surface 48 of locking ring 16 may include a groove or other structure 50 about all or a portion of the periphery of outer surface 48 for receiving retainer 18. A locking ring portal surface 52 together with portal surface 36 of shell 12 form the portal 54 or opening of prosthesis 10 through which head 20 and other portions of stem 24 extend. Some or all of portal surface 52 can include a surface of rotation or other modification 56 such as a chamfer or other non-curved or curved surface of rotation or a surface shaped as otherwise desired in order to improve clearance of stem 24 in portal 54 and thus increase range of motion of stem 24 relative to prosthesis 10. In the embodiment shown, FIGS. 1, 2, 6, 7 and 8, the surface 56 is a chamfer.

Locking ring portal surface 52 may transition through surface 56 or as otherwise desired to a capture surface 58 which forms the surface within prosthesis 10 of the least diameter about the center of rotation 46. Capture surface 58 of locking ring 16 may be, in cross-section, considered as cylindrical, rounded, or even a cusp. In any event, capture surface 58 of locking ring 16 which helps form the portal 54 in locking ring 16 and the prosthesis 10 is preferably substantially smaller in diameter about axis of rotation 46 than the largest diameter of stem head 20 about that axis (in all relevant desired orientations). As a result, when stem head 20 is captured within prosthesis 10, portions of locking ring 16 and in any event capture surface 58, form the mechanical structure which precludes or reduces dislocation of stem 24 from prosthesis 10.

Locking ring 16 also preferably includes an inner bearing surface 32 adapted to cooperate with head 20 in articulating relationship. Bearing surface 32 may be formed as surface of rotation with curvature corresponding generally to that of the stem head 20, and it may be surfaced as desired for optimal wear and mechanical properties.

The inner bearing surface 32 and its relationship to stem head 20 is important, because locking ring 16 and in particular inner bearing surface 32 absorb a substantial portion of tensile stress between stem 24 and prosthesis 10 such as that which would cause dislocation. Inner bearing surface 32 of locking ring 16 thus needs to be shaped and surfaced to reflect its reduced surface area which cooperates against stem head 20 in order to absorb the tensile load properly and optimally and to transfer it through locking ring 16 and retainer 18 to and through shell 12, without unnecessary motion between locking ring 16 and shell 12.

Figure 2:
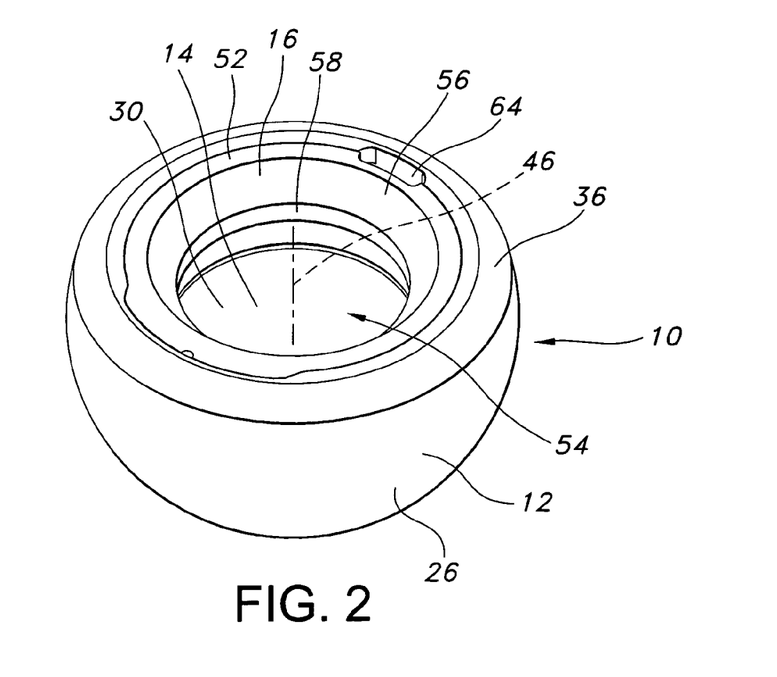
FIG. 2 is a perspective view of the prosthesis of FIG. 1.
Figure 3:
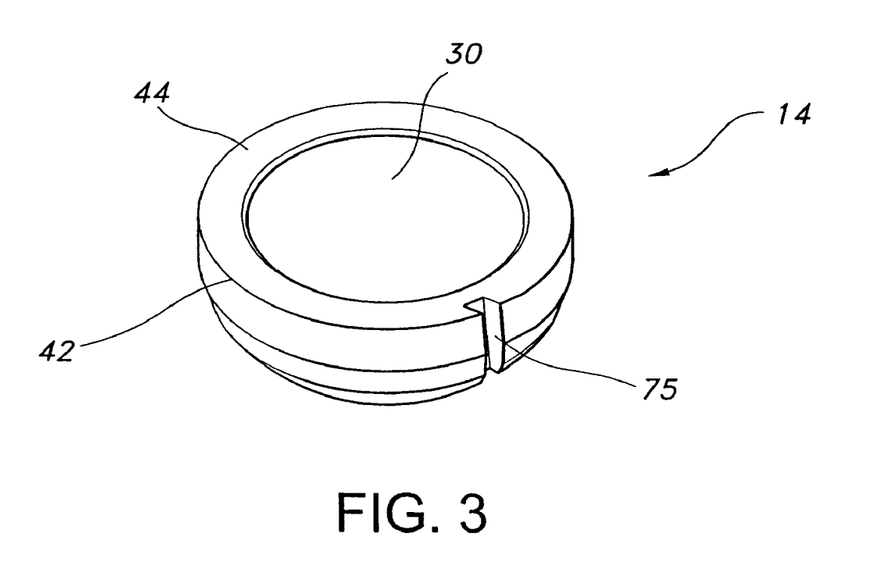
FIG. 3 is a perspective view of the liner of the prosthesis of FIG. 1.
Figure 4:
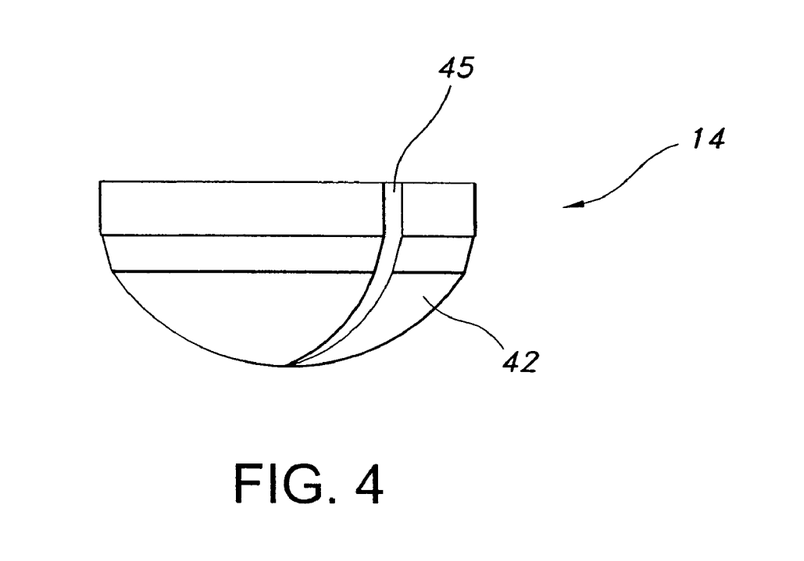
FIG. 4 is a side elevational view of the liner of FIG. 3.
Figure 5:
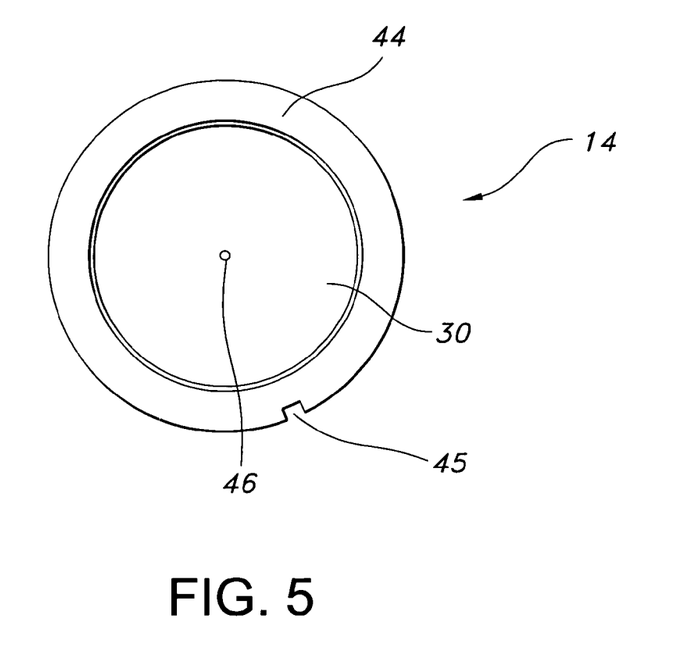
FIG. 5 is a plan view of the liner of FIG. 3.
Figure 6:
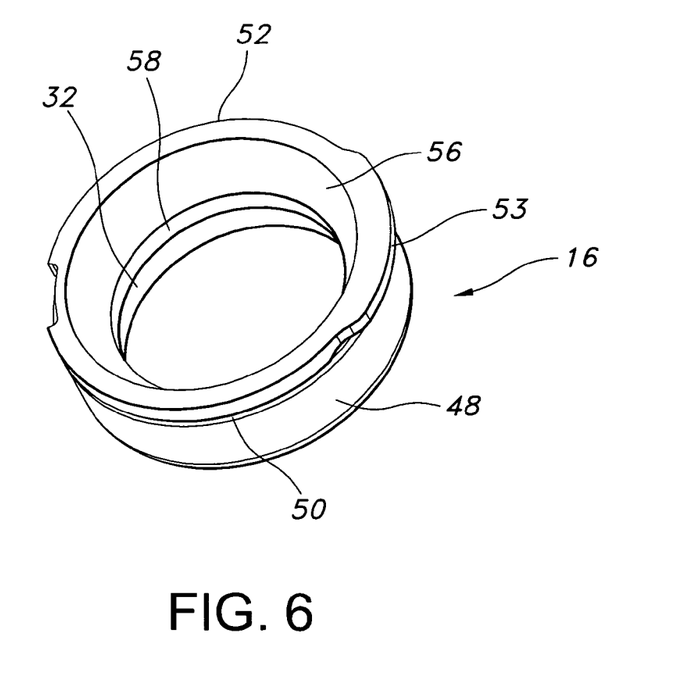
FIG. 6 is a perspective view of the locking ring of FIG. 1.
Figure 7:
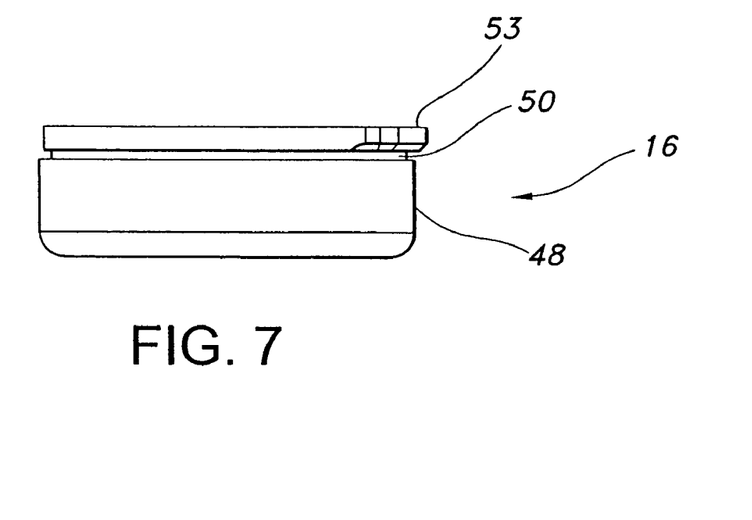
FIG. 7 is a side elevational view of the locking ring of FIG. 6.
Figure 8:
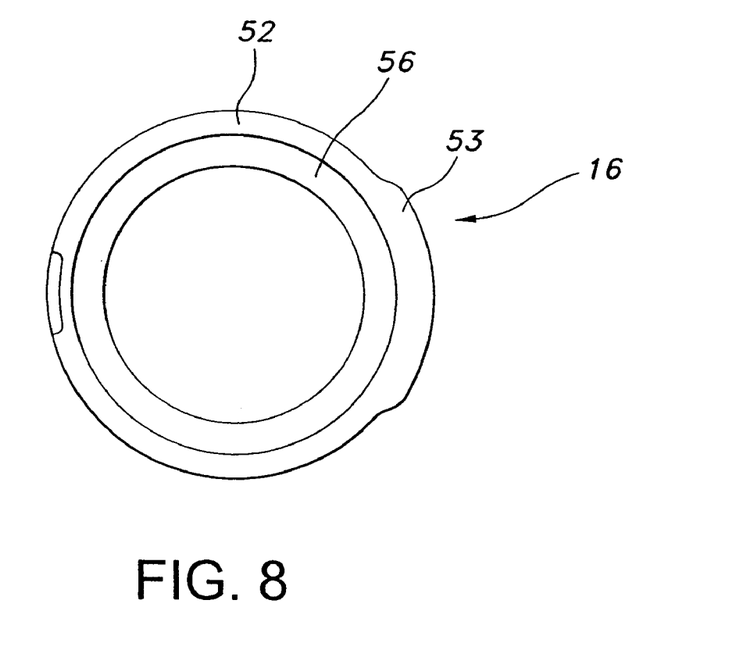
FIG. 8 is a plan view of the locking ring of FIG. 6.

Locking ring 16 is retained in and restrained in movement (at least in a direction parallel to axis of rotation 46) by retainer which fits within locking ring groove 50 and also a groove 62 formed in cavity 38 of shell 12. Locking ring 16 may be formed of spring or other memory retaining metal and preferably fits closely to the shape of grooves 50 and 62, no matter what shape they may assume, to stabilize, restrain, and cause capture of locking ring 16 within shell 12 in an optimal fashion to, among other things, preclude pistoning of stem 24 and movement of liner 14. As shown in FIG. 2, an access 64 may be formed in shell portal surface 36 and/or liner portal surface 52 in order to access and manipulate retainer 18. In the preferred embodiment, retainer 18 may be a C-ring so that it can be compressed, and locking ring 16 and therefore stem 24 can be removed for disassembly or access.

Figure 9:
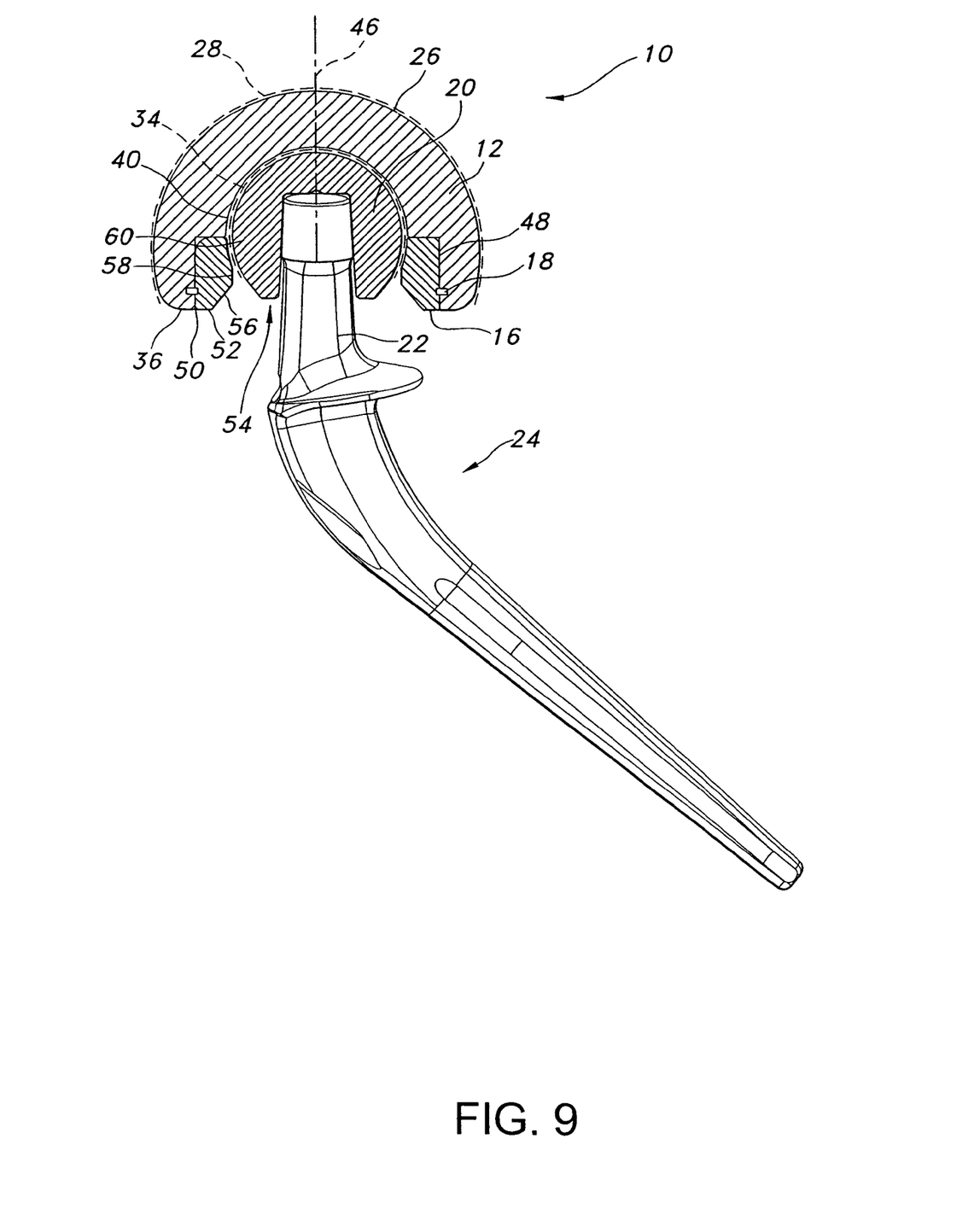
FIG. 9 is a schematic view of another embodiment of a prosthesis according to certain aspects of the present invention.

FIG. 9 shows a prosthesis 10 having a unitary design, without a liner. Here, head 20 of stem 24 fits directly within cavity 38 of shell 12 to form inner bearing 34. In this structure, head 20 may be of ceramic or metallic structure to cooperate with ceramic, metal, polyethylene shell 12 or shell 12 formed of another material. Configuration and operation of locking ring 16 and retainer 18 may be similar to that shown in FIG. 1. Locking ring 16 may be formed of ceramic, metal, polyethylene or any other desired material. Dislocation of stem 24 from prosthesis 10 is prevented or reduced by the reduced size of opening 54 by virtue of the non-split locking ring which is adapted to be assembled onto the neck 22 of the stem before the head 20 is mounted on the stem.

b. Treatment or Formation of Prosthetic Components to Improve, Accentuate or Optimize Properties such as Material Wear or Resistance to Dislocation.

Treating or forming components or portions of them according to certain aspects of certain embodiments of the present invention in order to improve, accentuate or optimize properties such as, for instance, wear performance, and other components or portions of them in order to improve, accentuate or optimize other properties, such as, for instance, mechanical properties, is relevant to prosthetic implants in general, but particularly to hip prosthetic components including total hip replacement components, bipolar prosthetic components, unipolar components, and versions of any of these which include a shell, a combination of a shell and liner, a combination of a shell, liner and locking ring, or any other desired combination of components. Materials which can be the subject of such differential treatment or formation include not only polyethylene components, but also ceramic and metal components as well as components formed of any other desired material. The bipolar structure disclosed and shown in the drawings is therefore only a subset of the aspects of the invention having to do with such treatment or formation, and that disclosure and those drawings should not be interpreted or construed to read artificial structural limitations, such as limitations to a bipolar prosthetic component, into the invention or certain aspects of it.

As a first example of these aspects of the invention, consider a prosthesis which includes a polyethylene component. It is generally recognized that treating polyethylene such as ultra high molecular weight polyethylene in order to cross-link it, such as by irradiation before, during or after forming the article into shape, significantly and radically reduces polyethylene wear including polyethylene particle generation rates and volumetric wear rates. However, such treatment can also substantially alter mechanical properties of the polyethylene as shown in the following Table 1 which are results obtained from testing according to ASTM Standards D638 (yield strength, tensile strength and elongation testing) and ASTM F648 (impact strength testing) which are incorporated herein by this reference.

MECHANICAL PROPERTIES

|  | Yield Strength (Mpa) | Tensile Strength (Mpa) | Elongation (%) | Impact Strength (kJ/m$^2$) |
| --- | --- | --- | --- | --- |
| Non-XL | 22.2 | 48.2 | 390 | 96.1 |
| 5 Mrad | 20.4 | 42.1 | 289 | 82.16 |
| 10 Mrad | 21.0 | 37.1 | 237 | 69.4 |

According to this example, a total hip replacement acetabular component of conventional structure such as that shown in U.S. Pat. No. 5,310,408 entitled Acetabular Cup Body Prosthesis, Schryver et al. inventors, issued May 10, 1994, which is incorporated herein by this reference, can feature a polyethylene liner which is formed of differentially treated polyethylene according to these aspects of the invention. Thus, portions of the liner nearer the axis of rotation, and thus deeper within the component and thus which can be expected to bear a greater load from the femoral stem head, can be treated to improve, accentuate or optimize wear performance such as irradiation or other treatment to improve cross linking or wear performance. Portions nearer the lip which have more to do with retaining the femoral stem head in the liner and thus inhibiting dislocation of the head can feature reduced or no such treatment in order to improve, accentuate or optimize (here, retain) mechanical properties such as yield strength, tensile strength, elongation properties, and impact strength.

As a second example, in a bipolar prosthesis that features a shell, a liner and a locking ring, such as the embodiment shown in FIG. 1, polyethylene that improves, accentuates or optimizes wear properties such as polyethylene that has been irradiated or cross linked to a desired degree can be used in the liner 14 as opposed to the locking ring 16, which improves, accentuates or optimizes mechanical properties having to do with, for example, inhibiting dislocation of a femoral stem head. Alternatively, the nature and treatment of the polyethylene or other material may be varied in various portions of the liner 14, and various portions of the locking ring 16, and, for bipolar prostheses where no locking ring is used, in the liner 14. The bipolar prostheses suitable for such differential polyethylene treatment or formation need not include a locking ring, and if they do, that locking ring can be split or configured as desired. In such prostheses without a locking ring, the liner 14 is adapted for the stem head to be forced into the liner before or after the liner is inserted or placed into the shell.

In alternative embodiments of bipolar prostheses according to this example which include liners and locking rings, various portions such as annular portions of the liner and locking ring may be treated as desired to improve, accentuate or optimize wear resistance and mechanical properties for optimal performance relative to the loads expected and received at those locations. For instance, concentric portions of the liner in the vicinity of axis of rotation may receive higher wear resistance treatment and portions toward the lip or opening of the liner may feature treatment or varying degrees of it which optimize the mechanical properties mentioned above in order, among other things, to reduce potential of femoral stem head dislocation. The treatment may be continuous from one location to the next, or it may be discontinuous. In bipolar structures in which no locking ring is employed, various portions of the liner may be treated as desired to optimize wear resistance on the one hand and the mechanical properties mentioned above on the other hand. Again, the treatment may vary from one location to the next in a continuous or discontinuous fashion or as otherwise desired.

In a narrower example, the inventors have found it advantageous in the preferred embodiment shown in FIG. 1 to form the locking ring 16 of generally non cross-linked ultra high molecular weight polyethylene while the liner 14 is formed of ultra high molecular weight polyethylene stock that has been treated using irradiation techniques to improve cross-linking. The shell and/or the femoral stem head can feature a surface that includes oxidized zirconium (as can components in any of the total hip replacement, bipolar, unipolar or other prostheses with which differential material treatment or formation according to these aspects of the invention are suitable.) Consequently, liner 14, which is generally absorbing the motion and wear from and imposed by head 20 of stem 24, is formed of the polyethylene that features better wear resistance. This improved wear resistance is significant, for the load imposed on liner 14 by head 20 can be three times body weight at a rate of one million or more cycles per year in the normal human. By contrast, the locking ring 16, which typically absorbs only loads caused by tendency of the stem 24 to withdraw through portal 54, can be made of polyethylene where wear resistance is perhaps less of an issue than the ability of the locking ring 16 to retain head 20 in the prosthesis 10 by virtue of higher yield strength, tensile strength, elongation, impact strength, and other mechanical properties having to do with robustness, reduced deformation, and as otherwise desired.

Various changes, modifications, additions, and/or deletions can be made to embodiments according to aspects of the present invention disclosed above without departing from this scope or spirit of the invention.

What is claimed is:

1. A bipolar prosthesis, comprising;
   a. a shell which includes an outer surface for bearing against acetabular tissue, a cavity and a shell portal surface interposed between the shell outer surface and the shell cavity, whereby the shape of the shell outer surface is deeper than hemispherical;
   b. a liner adapted to fit within the shell cavity, the liner containing a liner cavity adapted to receive a head of a femoral component;
   c. a continuous, non-split locking ring adapted to fit entirely within the shell cavity in order to retain the head of the femoral component within the liner cavity, the locking ring including a locking ring portal surface abutting the shell portal surface to form a portal for the liner inner cavity through which a head and other portions of a femoral component are adapted to extend, whereby the locking ring is adapted to physically lock a head of a femoral component in the liner cavity;
   d. wherein the liner includes a first portion of polyethylene which has been treated to improve its crosslinking and wear resistance properties, and the locking ring includes a portion of polyethylene which has not been treated to improve its cross linking and wear resistance properties, said portion of the locking ring thereby featuring greater strength properties than said treated portion of the liner, wherein the shell cavity and the locking ring each contain a groove; and
   e. a retainer adapted to be captured in the grooves of the shell cavity and the ring in order to retain the locking ring in the shell.

2. A prosthesis according to claim 1 in which the shell cavity and the locking ring each include at least one irregularity, which irregularities are adapted to cooperate in order to reduce relative motion of the ring relative to the shell.

3. A prosthesis according to claim 1 in which the shell cavity and the liner each include at least one irregularity, which irregularities are adapted to cooperate in order to reduce relative motion of the liner relative to the shell.

4. A prosthesis according to claim 1 in which the locking ring defines a continuous, non-split annulus which forms an opening to receive a neck of a femoral component, a diameter of the opening sufficiently small to mechanically prevent passage of a head of said femoral component through the ring.

5. A prosthesis according to claim 1 further comprising a femoral component.

6. A method for installing a bipolar prosthesis, comprising:
   a. providing bipolar prosthetic components including:
      1. a femoral component, comprising a stem, a neck and a head;
      2. a shell having an outer surface adapted to bear against acetabular tissue in on articulating relationship;
      3. a liner;
      4. a locking ring defining a continuous, non-split annulus which forms on opening to receive the neck of the femoral component, a diameter of the opening sufficiently small to mechanically prevent passage of the head of the femoral component through the ring: and
      5. a retainer;
   b. installing the shell in a patient's acetabulum;
   c. installing the femoral component in the patient's femur:
   d. inserting the neck of the femoral component through the locking ring and then mounting the head of the femoral component on the neck;
   e. inserting the head of the femoral component into the liner; and
   f. deploying the retainer to capture the locking ring in the shell in order to preclude escape of the femoral component head from the shell.

* * * * *